United States Patent
Gunjal et al.

(10) Patent No.: US 7,615,571 B2
(45) Date of Patent: Nov. 10, 2009

(54) PROCESS FOR MANUFACTURE OF PURE (2S, 3AS, 7AS)-1-[(2S)-2-[[(1S)-1-(ETHOXYCARBONYL)BUTYL]AMINO]-1-OXOPROPYL]OCTAHYDRO-1H-INDOLE-2-CARBOXYLIC ACID AND ITS TERT. BUTYL AMINE SALT

(75) Inventors: Sanjay Tukaram Gunjal, Mumbai (IN); Dilip Uttam Jadhav, Mumbai (IN); Ashok Kumar, Mumbai (IN); Mathur Arpana, Thane (IN); Nalinakshya Balaram Panda, Thane (IN); Satish Rajanikant Soudagar, Mumbai (IN)

(73) Assignee: IPCA Laboratories Ltd., Mumbai (IN)

( * ) Notice: Subject to any disclaimer, the term of this patent is extended or adjusted under 35 U.S.C. 154(b) by 170 days.

(21) Appl. No.: 11/324,349

(22) Filed: Jan. 3, 2006

(65) Prior Publication Data

US 2007/0021490 A1 Jan. 25, 2007

Related U.S. Application Data

(63) Continuation-in-part of application No. 11/140,226, filed on May 27, 2005, now abandoned.

(30) Foreign Application Priority Data

Jan. 6, 2005 (IN) .......................... 17.MUM.2005

(51) Int. Cl.
*A61K 31/403* (2006.01)
*C07D 209/12* (2006.01)

(52) U.S. Cl. ..................................... 514/412; 548/452
(58) Field of Classification Search ................ 548/452; 514/412

See application file for complete search history.

(56) References Cited

U.S. PATENT DOCUMENTS 7,179,833 B2 * 2/2007 Dubuffet et al. ............ 514/412

* cited by examiner

*Primary Examiner*—Golam M Shameem
(74) *Attorney, Agent, or Firm*—Blank Rome LLP

(57) ABSTRACT

New compounds useful as synthetic intermediates to synthesize perindopril, a new process for synthesizing perindopril, and new salts of perindopril.

15 Claims, No Drawings

PROCESS FOR MANUFACTURE OF PURE (2S, 3AS, 7AS)-1-[(2S)-2-[[(1S)-1-(ETHOXYCARBONYL) BUTYL]AMINO]-1-OXOPROPYL] OCTAHYDRO-1H-INDOLE-2-CARBOXYLIC ACID AND ITS TERT. BUTYL AMINE SALT

RELATED APPLICATIONS

This application claims priority from India national patent application Serial No. 17/MUM/2005, filed 06 Jan. 2005. This application is a continuation-in-part of Applicant's prior U.S. application Ser. No. 11/140,226, filed 27 May 2005 now abandoned.

FIELD OF INVENTION

The present invention relates to a new process for the manufacture of (2S, 3aS, 7aS)-1-[(2S)-2-[[(1S)-1-(ethoxycarbonyl)butyl]amino]-1-oxopropyl]octahydro-1H-indole-2-carboxylic acid commonly known as Perindopril, its salts like tert. butyl amine salt and its novel intermediate compounds, specifically aralkyl perindopril ester salts.

BACKGROUND AND PRIOR ART

Perindopril (Formula IA) and its pharmaceutically acceptable salts, especially the tert. butylamine salt (Formula IB), have valuable pharmacological properties. Their main property lies in the inhibition of the enzyme that converts angiotensin I (or kininase II), a precursor for formation of angiotensin II enzyme, thereby enables on the one hand prevention of the conversion of the decapeptide angiotensin I to the octapeptide angiotensin II (vasoconstrictor) and on the other hand prevention of the degradation of bradykinin (vasodilator) to inactive peptide. These two actions contribute to the beneficial effects of perindopril or its salts in cardiovascular disorders, especially arterial hypertension and cardiac insufficiency. The use of perindopril in these therapies demands high purity of the final compound in a manufacturing operation.

Perindopril, its preparation and its therapeutic use were first described in European Patent Specification No. 0049658.

An alternative route of synthesis for perindopril has been reported in Tetrahedron Letters 23, (16), 1677-1680, (1982), wherein the tert. butyl ester of (2S, 3aS, 7aS)-octahydroindole-2-carboxylic acid was coupled with N-[(S)-1-carboxybutyl]-(S)-alanine ethyl ester (Formula III) in presence of triethyl amine, dicyclohexylcarbdiimide(DCC), and 1-hydroxy benzotriazole(HOBT) and subsequently deprotecting the tert. butyl ester protective group from the resultant intermediate. The tert. butyl amine (erbumine) salt of perindopril was reported for the first time in the above publication.

Subsequently, European patent No. 0308341 has disclosed a similar process for perindopril claimed to be an industrial process by the reaction of (2S, 3aS, 7aS)-octahydroindole-2-carboxylic acid esters of Formula II with N-[(S)-1-carboxybutyl]-(S)-alanine ethyl ester of Formula III using triethylamine, DCC and HOBT to give the compound of Formula IV followed by de-protection of ester group selectively by methods known in the art to get perindopril (Formula IA). The ester forming groups for (2S, 3aS, 7aS)-octahydroindole-2-carboxylic acid ester are selected from benzyl, and alkyl groups. Perindopril erbumine salt (Formula IB) is then obtained by combining tert. butylamine with Perindopril (Formula IA).

However, the product obtained by the above process contains many impurities thereby making the product isolation difficult even on laboratory scale, as also observed by others, and the process improvement taking care of a part of the problems has been the subject of patent applications No. U.S. 2003/0069431 and WO 0364388.

The United States patent application 2003/0069431 describes a modified process for the manufacture of Perindopril and its tert.-butyl amine salt using the same reactants. It discloses the reaction of benzyl ester of (2S, 3aS, 7aS)-octahydroindole-2-carboxylic acid with N-[(S)-1-carboxybutyl]-(S)-alanine ethyl ester in solvent ethyl acetate, in presence of reduced molar quantities of HOBT, DCC and in presence or absence of triethyl amine, whereby the impurities of Formula VII & Formula VIII in perindopril are brought down to below 0.1 and 0.2% respectively but with extra purifications.

Formula VII

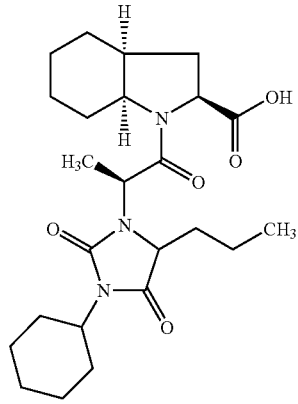

Formula VIII

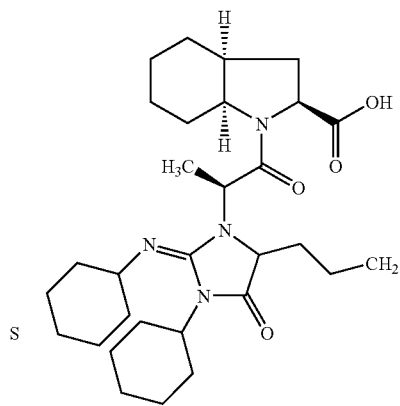

According to the process mentioned in patent application No. WO 03/064388, the compound of Formula III is N-protected by suitable carbonic acid derivatives. The carboxylic acid group is then converted into its acid chloride, followed by its reaction with octahydroindole-2-carboxylic acid, yielding perindopril of better purity. It also avoids use of DCC. Various other process-patents such as EP1371659, EP1380591, EP1380590, EP 1362864, EP1367061 are published, and claimed to minimize the problems associated with prior art i.e. purity of Perindopril. In these reports, the route of synthesis and the intermediates are different than the processes, discussed above.

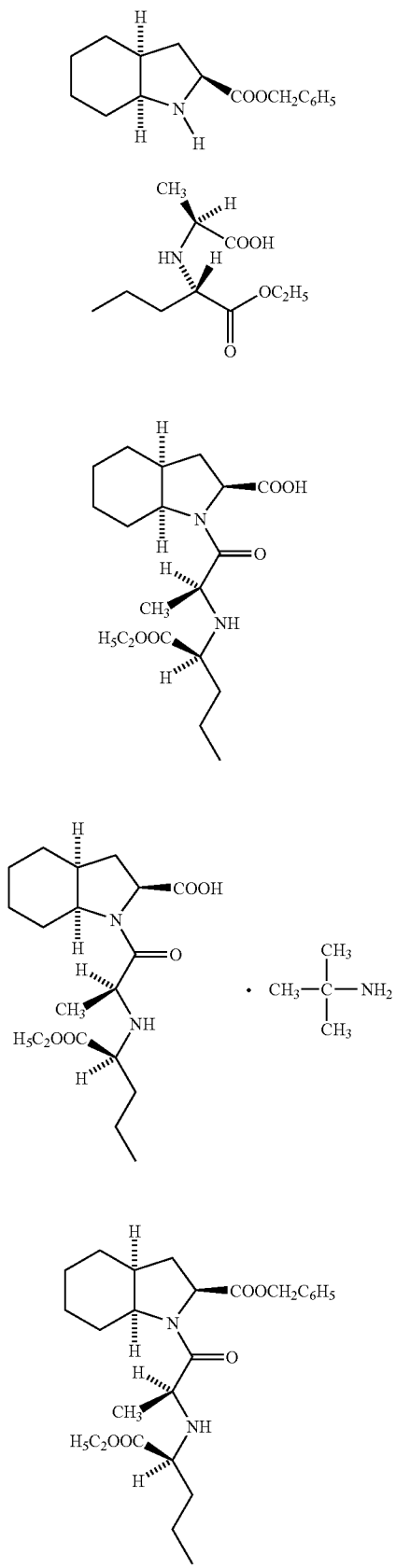

Formula II

Formula III

Formula IA

Formula IB

Formula IV

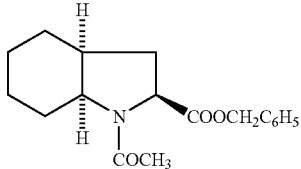

Formula V

A thorough study of prior art indicates that the process route disclosed in Tetraherdon Letters 1982, 23(16), 1677-1680, is the best suited as an industrial route and comparatively more economical to produce Perindopril or its erbumine salt, provided it avoids the formation of impurities as well as eliminates need for additional purification steps. Patent application WO 01/58868 addressed this problem to some extent by reducing two impurities having Formula VII and VIII to give improved quality of the product.

The processes mentioned in patents EP 0308341 and WO 01/58868 describe the use of ethyl acetate as a solvent in the amino acid coupling step. Under the conditions of coupling, one major impurity, viz. N-acetyl (2S, 3aS, 7aS)-octahydroindole-2-carboxylic acid benzyl ester (Formula V), is formed. Formation of this impurity has been identified to be associated with the use of ethyl acetate as solvent. The reason being ethyl acetate acting as acylating agent to form the impurity of Formula V. Removal of this impurity is very difficult at this stage, as the nature of the impurity and the resultant coupled products is very similar. It is also difficult to remove the impurity in the next step i.e. debenzylation. The coupled product (Formula IV) gives Perindopril (Formula IA) whereas compound of Formula V also gets debenzylated to form N-acetyl (2S, 3aS, 7aS) octahydroindole-2-carboxylic acid (Formula VI), which again contaminates as an impurity in final perindopril. Since the heterocyclic part containing the carboxylic acid group is present in both Perindopril (Formula IA) and in this impurity (Formula VI) and due to this, during salt formation of Perindopril with tert.-butylamine, compound of Formula VI invariably remains contaminated with the final perinodpril erbumine salt (Formula IB).

Formula VI

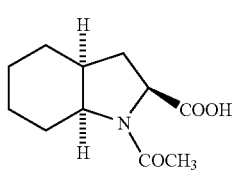

Yet another report (WO 2004/099138), disclosed a debenzylation of benzylperindopril in presence of tert.butylamine to directly isolate perindopril erbumine salt after debenzylation. Although this process reduces one process operation, i.e., tert. butylamine salt formation, but the process does not take care of impurities generated in the peptide coupling stage, i.e., the benzyl perindopril formation and there is no report on the effective means for purification of the product. This again leads to repeated purification of the final perindopril erbumine salt to get a pharmaceutically acceptable purity.

Although the impurities formation can be controlled to some extent by varying solvents or by changing the coupling catalysts, but the problems of isolation & purification of the benzyl perindopril as well as resulting perindopril still remains. Since there is no effective means for a purification of benzyl perindopril, which is an oily product, it is difficult to ensure the purity of benzyl perindopril and thus that of perindopril. This eventually necessitates extra purifications in the tert. butyl amine salt formation stage, incurring heavy losses of the final product, perindopril erbumine.

From the above description it is clear that the key to the success of the process is the purity of benzyl ester of perindopril obtained after the coupling of intermediate compounds of Formula II & III. The present invention directs to address these problems, where a means for the isolation of benzylperindopril of Formula IV is provided to get rid of the impurities resulting from the peptide coupling reaction and thereby reflecting in high purity of perindopril erbumine, the subject of the present invention.

OBJECTIVE OF THE PRESENT INVENTION

The major objective of the present invention is to provide an industrial process, which gives high purity perindopril or its salts, and improvements thereof. A further objective is to provide suitable intermediate compounds useful for the synthesis of perindopril or its salt of high purity. Yet another objective is to provide a suitable process & methods for purification of benzyl perindopril to get higher purity in order to use in the synthesis.

SUMMARY OF THE INVENTION

Accordingly, in one aspect, the present invention provides novel aralkyl perindopril ester salts represented by the general formula IVA for the synthesis of perindopril erbumine. The acids capable of forming the salt of aralkyl ester of perindopril include organic (chiral & achiral) and inorganic acids. The examples of new salts of the present invention include, but not limited to, benzylperindopril phthalic acid salt, benzylperindopril tartaric acid salt, benzylperindopril phosphate, benzyl perindopril camphor sulphonate, benzylperindopril oxalate, benzylperindopril citrate, benzylperindopril (−)-di-p-toluoyl tartarate, benzylperindopril (+)-di-p-toluoyl tartarate, benzylperindopril (±)-dibenzoyltartarate or the like.

In a further aspect, the present invention relates to use of novel intermediate salts of aralkyl perindopril ester of the present invention for the synthesis of perindopril erbumine in pharmaceutically acceptable purity & higher yields.

In one more aspect, the present invention provides a process for preparation of aralkyl perindopril ester salts of Formula IVA, which process involves condensation of an aralkyl ester of octahydroindole of Formula IIA or its acid salt with the compound of Formula III in presence of a coupling reagent like DCC, triethyl amine and HOBT in a non-reactive solvent like methylene chloride to form a reaction mixture including aralkyl ester of perindopril, and treating the reaction mass containing aralkyl perindopril ester with an acid capable of forming a salt and isolating the aralkyl perindopril ester salt from the reaction mass as solid in higher HPLC purity. The aralkyl perindopril ester salt can be separated from the mixture by conventional means such as filtration, extraction, precipitation, centrifugation etc. and can be optionally purified at ambient or elevated temperatures.

In another embodiment of the present invention, the resulting intermediate aralkyl perindopril ester salt (Formula IVA) is deprotected under hydrogenation condition using metal catalyst such as palladium/C in solvents such as C1 to C4 straight or branched chain alcohols. The product is isolated as corresponding perindopril acid addition salt or either neutralized with a base to isolate free perindopril or directly converted to tertiary butylamine salt, i.e., perindopril erbumine.

In yet another embodiment of the present invention the perindopril erbumine salt is formed by combining the tert.butyl amine base with perindopril free acid or its acid addition salt in aqueous medium. The erbumine salt is isolated by extracting using a water immiscible organic solvent, concentration of the extraction solvent and optional leaching with a second organic solvent to obtain perindopril erbumine in pure form. In yet another aspect the invention relates to perindopril prepared according to the process of the present invention.

In a further aspect, the present invention provides pharmaceutical compositions containing high purity perindopril or its erbumine salt prepared according to the novel process described herein. The pharmaceutical compositions may contain additional ingredients commonly used in the preparation of such dosage forms such as fillers, binders, lubricants, stabilizers, disintegrants etc. The dosage forms may include tablets, capsules, lozenges, oral solutions/suspensions and injectables.

DETAILED DESCRIPTION

The present invention provides a novel process for preparation of perindopril erbumine salt of Formula IB in pure form, which ameliorates most of the problems associated with reported industrial processes. The method is simple, operates in moderate reaction conditions, yields high purity perindopril erbumine and easy to operate on industrial scale. A preferred embodiment of the present process is illustrated in scheme 1, which is presented below:

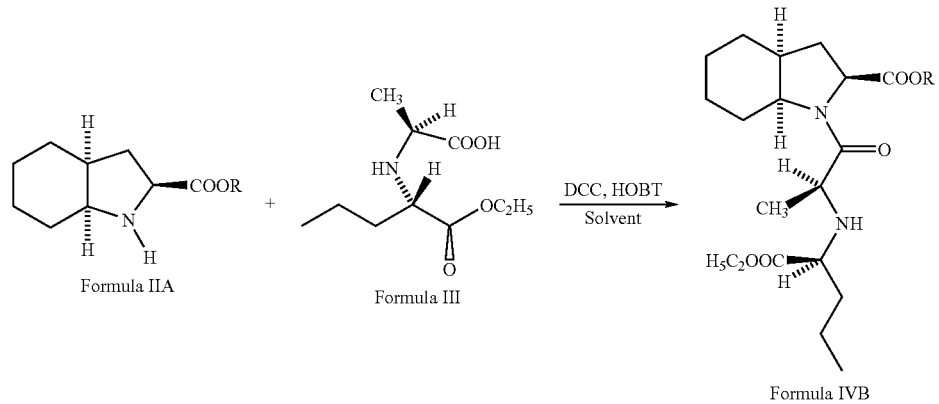

Scheme 1

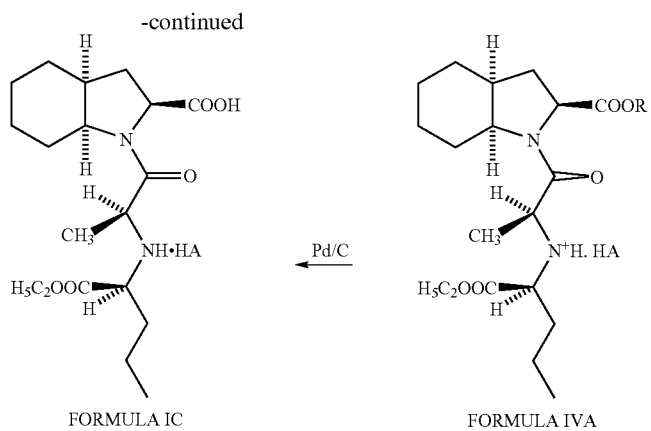

FORMULA IC      FORMULA IVA

In scheme 1, in Formula IIA, IVB & IVA, the R group is the corresponding substituted/un-substituted aralkyl groups (the terminology arylalkyl means to be synonym of aralkyl in this specification) that can be in each case substituted or un-substituted phenyl methyl groups. The preferred aralkyl groups are benzyl, mono- or di-, or tri-alkyl or alkoxy or halo or nitro substituted benzyl, diphenyl methyl, or triphenylmethyl or the like. Although there is no special limitation, the preferred aralkyl group is benzyl. For the purposes of illustration the 'R' group is explained with respect to benzyl group in the description detailed below.

In the scheme I, in Formula IVA the acid is selected from chiral or achiral organic acid and inorganic acids. If not stated specifically, the acids capable of forming salts of Formula IV may include mono-basic, dibasic, or polybasic acids. The preferred acids are selected from, but not limited to, phthalic acid, tartaric acid, di-p-toluoyl tartaric acid, dibenzoyl tartaric acid, camphor sulphonic acid, oxalic acid, citric acid, phosphoric acid and para-toluenesulphonic acid. The most preferred acid is oxalic acid or di-p-toluoyl tartaric acid. Consequently the above acid salts of perindopril alkyl/aralkyl ester of Formula IVA, exemplary salts include benzylperindopril phthalic acid, benzylperindopril tartrate, benzylperindopril phosphate, benzyl perindopril camphor sulphonate, benzylperindopril oxalate, benzylperindopril citrate, benzylperindopril (−)-di-p-toluoyltartarate, benzylperindopril (+)-di-p-toluoyl tartarate , benzylperindopril (±)-dibenzoyl tartarate, of the present invention are novel and forms part of the present invention.

Hence the present invention provides the novel salts of alkyl/aralky perindopril ester (Formula IVA) as intermediates for preparing perindopril or its salts in higher purity and yields. The process for perindopril or its salts of the present invention is further described in detail below:

In a preferred embodiment of the process of the present invention, a compound of Formula IA or IB is prepared by the process comprising, a) reacting octahydrocarboxyindole carboxylic acid ester (Formula IIA, where R is alkyl/aralkyl group) with a compound of Formula III, to obtain a compound of Formula IVB; and b) converting said compound to an acid addition salt of Formula IVA by reacting it with an acid capable of forming a salt and isolating the said salt of Formula IVA in substantially pure form, and c) further deprotecting the compound of Formula IVA to recover salt of perindopril with corresponding acid and further converting to the product of Formula IA or IB.

In the process, in a first step, the octahydroindole carboxylic acid ester of Formula IIA or its acid salt is reacted with the alanine derivative of Formula III in presence of peptide coupling reagents like DCC, HOBT and with or without a base like triethylamine . The acid salt of octahydroindole carboxylic ester is preferably a para-toluene sulphonate salt. The coupling reaction is preferably carried out in a non-reactive peptide coupling solvents selected from chlorinated hydrocarbon solvents, hydrocarbon solvents or polar aprotic solvents or ether solvents.

In a preferred embodiment of the present process, the para-toluene sulphonate salt of compound of Formula IIA is coupled with alanine derivative of Formula III in presence of DCC, HOBT and triethyl amine in solvents like methylene dichloride or the like. The reaction is preferably carried out by mixing the components in the non-reactive solvent media at a temperature of about 10 to 35° C. for a period of 12 to 24 hours. In the process the molar amount of reactants and reagents are optimized in order to minimize the impurity generation in the coupling stage. The preferred molar ratio of compound of Formula III to compound of Formula IIA is about 1.0 to 2.0 wherein the amounts of reagents DCC & HOBT are in a molar amount ranging from about 1.0 to 2.0 moles relative to compound of Formula IIA. Triethyl amine is used in molar proportion of 1.0 to 3.0 relative to compound of Formula IIA.

After completion of reaction the reaction mass containing aralkylperindopril ester is filtered to remove the by-product (dicyclohexyl urea). The remaining traces of dicylohexylurea from the reaction mass are removed by concentrating reaction solvent, dissolving the obtained residue in non-polar solvents like hexane, cyclohexane or diisopropyl ether and filtering out the residual dicyclohexylurea.

In the second step of the present invention, the oily intermediate aralkyl ester of perindopril obtained is combined with an organic or inorganic acid capable of forming a salt. The salt formation is preferably carried out in a solvent such as methylene chloride, or ketone solvents like acetone, or C1 to C4 alcohol, or the like. The organic acid used for the isolation of aralkyl perindopril ester salt is selected from, but not limited to, phthalic acid, L-(+)-tartaric acid, di-p-toluoyl tartaric acid, (±)-dibenzoyl tartaric acid, camphor sulphonic acid, oxalic acid, citric acid, phorsphoric acid, sulphonic acid such as methane sulphonic acid and para-toluenesulphonic acid The solvent especially useful during the salt formation includes alcohols, ethers, acetonitrile, ketonic solvents such as acetone, hydrocarbon solvents, and chlorinated hydrocarbon solvents.

In the above process, a sufficient quantity of acid is used to form the salt and is preferably in a molar amount ranging from 1 to 2 moles. Typically a slight excess of acid is used to ensure the complete salt formation and it is preferably about 1.0 to 1.8 moles relative to the starting compound of Formula IVB. The salts are preferably formed at ambient temperature conditions by agitating the mixture in the solvent for sufficient period of time or by means of heating the mixture in the solvent for sufficient period of time.

The aralkylperindopril ester salt (Formula IVA) is then isolated from the reaction solvent, and if required, further purified by conventional means like crystallization, or precipitating out using an anti-solvent & recrystallization or solvent evaporation and slurrification in a second solvent. Anti-solvent herein means a solvent where the required substance (solute) is insoluble or sparingly soluble so that the addition of such solvent brings out the product of choice from the more soluble solvent solution. The solvents especially useful for this purpose in this invention are hydrocarbon solvents like hexane, cyclohexane, toluene or the like.

The precipitated aralkyl perindopril ester salt can then be separated from the solvent(s) by conventional means such as filtration, centrifugation etc. and can be optionally dried at ambient temperatures. In most of the cases the purity of the isolated aralkyl perindopril ester salt exceeds 99% sufficient enough to produce pure perindopril erbumine. This higher purity of the intermediate essentially avoids further purification of perindopril or its salt after de-protection and thereby reduces subsequent losses. Moreover this improvement facilitates the isolation of either perindopril or perindopril salts in pure crystalline form.

Finally, according to the present invention, the aralkyl perindpril ester salt (IVA) is de-protected using conventional deprotection reagents to give perindopril or its salts. In a preferred embodiment of the invention, the isolated acid salt of aralkyl perindopril ester is hydrogenated using hydrogenation catalyst like palladium, to form perindopril or its salts. The deprotection process is preferably performed in a solvent medium selected from, but not limited to, C1 to C4 straight or branched chain alcohol or their mixture. The removal of aralkyl ester group is effected at a hydrogenation temperature in the range of 25 to 40° C. and under a hydrogen pressure of about 1 to 6 atmospheres. After deprotection the catalyst is removed by filtration, the filtrate after concentration gives the acid salt of perindopril. The acid salt of perindopril can be isolated after the deprotection in solid form or is carried forward for the erbumine salt formation directly in the extraction solvent.

The perindopril erbumine (Formula IA) is then prepared by cleavage of this salt using a base in an aqueous medium and extracting perindopril with the help of an organic solvent. The perindopril so obtained, after evaporation of extraction solvent, is combined with tertiary butylamine in a suitable solvent such as ethyl acetate, MDC or alcohols etc and crystallized to obtain perindopril erbumine salt. The base preferably used to break the perindopril acid salt is selected from alkali metal carbonate or bicarbonates or trialkyl amines.

Alternately, the perindopril acid salt obtained above is treated with an excess amount of tertiary butylamine in an aqueous medium. Perindopril erbumine salt thus obtained is then directly extracted with an organic solvent such as methylene chloride or the like. The pure perindopril erbumine salt (Formula IB) is then isolated either by removing the solvent or changing the extraction solvent with a second solvent such as ethyl acetate and crystallizing pure perindopril by applying cooling or chilling. The process of precipitation is also being carried out in a mixture of first and second solvent and in that case the second solvent acts as an anti-solvent. Anti-solvent herein means a solvent where the perindopril erbumine has less or poor or no solubility.

The precipitated perindopril erbumine salt can then be separated from the solvent mixture by conventional means such as filtration, centrifugation etc. and can be optionally dried at ambient or elevated temperatures. The purity of perindopril erbumine is at least 99.5% by following this process.

In a process variant, according to the invention, in the hydrogenation step of aralkyl perindopril ester salt (Formula IVA), a hydrogenation composition is made by combining aralkyl perindopril ester salt, a base, a palladium catalyst and an organic solvent, which is subjected to hydrogenation conditions. In this step the base is preferably tertiary butyl amine and is used in sufficient quantity to form the perindopril erbumine salt after hydrogenation. The base is preferably used in a molar amounts ranging from 1 to 4 moles equivalents relative to the aralkyl perindopril ester salt. This process variant has advantages that it either neutralizes the reaction mixture to liberate perindopril free acid or make the perindopril erbumine salt directly without having the need of an additional step for salt formation. The perindopril erbumine salt obtained is further crystallized from ethyl acetate.

The advantage of making an acid addition salt of aralkyl perindopril according to this invention is that various impurities, both polar and non-polar, can be removed very efficiently. Additionally, this isolation of intermediate in crystalline form facilitates the removal of other chiral isomers and yields the benzylperindolpril ester salt and final perindopri-late or perindopril erbumine in higher chiral purity.

The following examples, which include preferred embodiments, will serve to illustrate the practice of this invention, it being understood that the particulars shown are by way of example and for purpose of illustrative discussion of preferred embodiments of the invention.

EXAMPLES

Example 1

(2S, 3aS, 7aS)-1-{(2S)-2-(1S)-1-(Ethoxycarbonyl)-butylamino]-propionyl}-octahydro-1H-indole-2-benzyl carboxylate (Benzyl perindopril)

To a suspension of 100 gm. of para-toluene sulfonate of benzyl ester of (2S, 3aS, 7aS)-octahydroindole-2-carboxylic acid in 2.0 liter of methylene chloride, 70.3 gm of triethylamine is added at 20-25° C. After stirring, 34.5 gm of 1-hydroxybenzotriazole, 60.4 gm. of N-[(S)-carbethoxy-1-butyl] 1(S)-alanine and 57.4 gm. of dicyclohexylcarbodiimide were added in the same sequence at the interval of about 15 minutes. The heterogeneous mass is stirred till completion of reaction at 20-25° C. Then the dicyclohexyl urea is filtered and the filtrate is washed with water. The solvent is removed under vacuum. Approx. 1.0 liter of disopropyl ether is added to the above mass and stirred for about 15 minutes, filtered, solvent distilled under vacuum to give 105 gm. (99%) product in the form of oil (purity 90%).

Example 2

Benzylperindopril Oxalate

In a reaction flask, 20 gm of the oil obtained as per Example 1 was taken in 60 ml dichloromethane. 7.07 gm of oxalic acid was added and mixed at ambient temperature for about 2-3 hours. To this mixture 500 ml of hexane was added and further maintained under stirring for about 2 hours. The solid obtained was filtered and dried to obtain 24.5 gm of oxalic acid salt of benzyl perindopril. (melting point 108-118° C.).

Example 3

Perindopril Oxalate 15 gm of oxalic acid salt of benzyl perindopril obtained as per Example 2 was taken in 150 ml ethanol in an autoclave. 1.5 gm of 5% Pd/C catalyst was charged to the autoclave and debenzylation was carried out at about 5 kg/cm$^2$ hydrogen pressure at around 30° C. Debenzylation was completed in 3-4 hours and then the catalyst was filtered and the filtrate was distilled to remove solvent to obtain 12.0 gm of oxalic acid salt of perindopril.

Example 4

Perindopril Erbumine 10 gm of oxalic acid salt of benzyl perindopril obtained as per Example 2 was taken in 200 ml ethanol and mixed with 5.0 gm tert.butyl amine. The mixture was charged to an autoclave. 1.0 gm of 5% Pd/C catalyst was charged to the autoclave and debenzylation was carried out at about 5 kg/cm$^2$ hydrogen pressure at around 30° C. Debenzylation was completed in about 3 hours and then the catalyst and insoluble salt were filtered and the filtrate was distilled to remove solvent. The residue was crystallized from ethyl acetate to obtain 5.0 gm of Perindopril erbumine.

Example 5

Perindopril Erbumine

To 10 gm of oxalic acid salt of perindopril obtained as per Example 3, 100 ml of dichloromethane was added and mixed with 9.3 ml of tert.butylamine. Upon agitation a thick mass was precipitated out which was filtered off. The filtrate obtained was then distilled to remove solvent. The solid obtained was dissolved in 150 ml of ethyl acetate at reflux temperature and then cooled to 30° C. The precipitate was filtered to obtain 4.9 gm of perindopril erbumine.

Example 6

Perindopril Erbumine

To 10 gm of oxalic acid salt of perindopril obtained as per Example 3, 30 ml water was added. To this 8.0 gm of tert-butylamine was added. The perindopril erbumine salt obtained was extracted into dichloromethane from the aqueous layer. The organic layer was then distilled to remove solvent. The residue obtained was dissolved in 100 ml ethyl acetate at reflux temperature. The solution was cooled and filtered to give 4.8 gm of perindopril erbumine.

Example 7

Perindopril Erbumine 20 gm of oxalic acid salt of benzyl perindopril obtained as per Example 2 was taken in 200 ml ethanol in an autoclave. 2.0 gm of 5% Pd/C catalyst was charged to the autoclave and debenzylation was carried out at about 5 kg/cm$^2$ hydrogen pressure at around 30° C. Debenzylation was completed in about 3 hours and then the catalyst was filtered off. To the filtrate 12 gm of tert.butyl amine was added and the precipitated salt was filtered. The filtrate was distilled to remove solvent and the residue was crystallized from 200 ml of ethyl acetate to obtain 10.0 gm of Perindopril erbumine

Example 8

(−)-DPTTA Salt of Benzyl Perindopril

In the reaction flask, 20 gm of the oil obtained as per Example 1 was taken in 200 ml acetone. To this 20 gm of (−)-di-p-toluoyl tartaric acid [(−)-DPTTA] was added and mixed at ambient temperature for about 2-3 hours. Then acetone was distilled and 400 ml of hexane was added and further maintained under stirring for 2 hours. The precipitate was filtered and dried to obtain 38.9 gm of (−)-di-p-toluoyl tartaric acid salt of benzyl perindopril i.e. (−)-DPTTA salt of benzyl perindopril (melting point 69-74° C.).

Example 9

Perindopril (−)-DPTTA Salt 15 gm of (−)-DPTTA salt of benzyl perindopril obtained as per Example 8 was taken in 150 ml ethanol in an autoclave. 1.5 gm of 5% Pd/C catalyst was charged in the autoclave and debenzylation was carried out at about 5 kg/cm$^2$ hydrogen pressure at ambient temperature. Debenzylation was completed in about 3 hours and then the catalyst was filtered and the filtrate was distilled to remove solvent. 150 ml of cyclohexane was added to the residue and a slurry was prepared in cyclohexane and stirred for 2 hours. The solid was filtered to obtain 13.5 gm of (−)-di-p-toluoyl tartaric acid salt of perindopril i.e. (−)-DPTTA salt of perindopril.

The crude product was crystallized from ethyl acetate-hexane mixture (1:1.5) to obtain 9.0 gm of pure (−)-di-p-toluoyl tartaric acid salt of perindopril i.e. (−)-DPTTA salt of perindopril. (melting point 150-153° C.).

Similar to Example 6, perindopril erbumine was prepared from 10 gm of (−)-DPTTA salt of perindopril obtained as per above example (yield 3.2 gm).

Example 10

(+)-DPTTA Salt of Benzylperindopril

In the reaction flask, 20 gm of the oil obtained as per Example 1 was taken in 200 ml acetone. To this 20 gm of (+)-di-p-toluoyl tartaric acid [(+)-DPTTA] was added and mixed at ambient temperature for about 2-3 hours. Then acetone was distilled and 400 ml of hexane was added and further maintained under stirring for 2 hours. The precipitate was filtered and dried to obtain 38.9 gm of (+)-di-p-toluoyl tartaric acid salt of benzyl perindopril i.e. (+)-DPTTA salt of benzyl perindopril

Example 11

Perindopril-(+)-DPTTA Salt 20 gm of (+)-DPTTA salt of benzyl perindopril obtained as per Example 10 was taken in 200 ml ethanol in an autoclave. 2.0 gm of 5% Pd/C catalyst was charged in the autoclave and debenzylation was carried out at about 5 kg/cm$^2$ hydrogen pressure at ambient temperature. Debenzylation was completed in about 3 hours and then the catalyst was filtered and the filtrate was distilled to remove solvent. 200 ml of cyclohexane was added into the residue and a slurry was made in cyclohexane and stirred for 2 hours. The solid was filtered to obtain 16.8 gm of (+)-di-p-toluoyl tartaric acid salt of perindopril i.e. (+)-DPTTA salt of perindopril (melting point 86-92° C.).

Example 12

(±)-DBTA Salt of Benzyl Perindopril

In the reaction flask, 15 gm of the oil obtained as per Example 1 was taken in 150 ml of dichloromethane. To this 14 gm of (±)-dibenzoyl tartaric acid (DBTA) was added and mixed at ambient temperature for about 2-3 hours. Dichloromethane was distilled and 400 ml of hexane was added and further maintained under siring for 2 hours. The precipitate was filtered and dried to obtain 29 gm of (±)-dibenzoyl tartaric acid salt of benzyl perindopril i.e. (±)-DBTA salt of benzyl perindopril Example 13

Perindopril-(±)-DBTA Salt 15 gm of. (±)-DBTA salt of benzyl perindopril obtained as per Example 12 was taken in 150 ml ethanol in an autoclave. 1.5 gm of 5% Pd/C catalyst was charged to the autoclave and debenzylation was carried out at about 5 kg/cm$^2$ hydrogen pressure at ambient temperature. Debenzylation was completed in about 3 hours. The catalyst was filtered and the filtrate was distilled to remove solvent to obtain 13.4 gm of (±)-dibenzoyl tartaric acid salt of perindopril i.e. (±)-DBTA salt of perindopril Example 14

Perindopril Tartarate (a) In the reaction flask, 10 gm of the oil obtained as per Example 1 was taken in 150 ml of acetone. To this 3.6 gm of L-(+)-tartaric acid was added and mixed at reflux temperature for about 2-3 hours. Acetone was distilled to obtain 13.5 gm of tartaric acid salt of benzyl perindopril.

(b) 9.0 gm of tartaric acid salt of benzyl perindopril obtained above was taken in 100 ml ethanol in an autoclave. 1.5 gm of 5% Pd/C catalyst was charged to the autoclave and debenzylation was carried out at about 5 kg/cm$^2$ hydrogen pressure at ambient temperature. Debenzylation was completed in about 3 hours. The catalyst was filtered and the filtrate was distilled to remove solvent to obtain 7.5 gm of tartaric acid salt of perindopril.

Example 15

Perindopril from Benzylperindoprilphosphate (a) In the reaction flask, 25 gm of the oil obtained as per Example 1 was taken in 250 ml acetone. To this 7.5 gm of ortho phosphoric acid was added and mixed at ambient temperature for about 2-3 hours. Then acetone was distilled out to obtain 31 gm of phosphate salt of benzyl perindopril.

(b) 30 gm of phosphate salt of benzyl perindopril obtained above was taken in 300 ml of ethanol and charged in an autoclave. 3 gm of 5% Pd/C catalyst was charged to the autoclave and debenzylation was carried out at about 5 kg/cm$^2$ hydrogen pressure at ambient temperature. Debenzylation was completed in about 3 hours, then the catalyst was filtered and the filtrate was distilled to obtain 25.3 gm of phosphate salt of perindopril.

(c) 7.0 gm of phosphate salt of perindopril obtained above was taken in 21 ml of water. To this 6.7 ml of tert. butyl amine was added. It was stirred for 1 hour at ambient temperature and then perindopril erbumine was extracted in dichloromethane. The solvent was distilled and the residue obtained was dissolved in 75 ml ethyl acetate at reflux temperature. The solution was cooled and precipitated solid was filtered to get 3.8 gm of perindopril erbumine.

We claim:

1. A compound of general formula IVA,

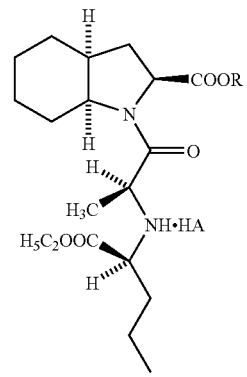

Formula IVA wherein R is an aryl alkyl group and wherein HA represents an acid capable of forming a salt.

2. The compound as claimed in claim 1, wherein said aryl alkyl group is selected from the group consisting of benzyl; alkyl-substituted benzyl; alkoxy-substituted benzyl; halo-substituted benzyl; nitro-substituted benzyl; diphenyl methyl; or triphenylmethyl.

3. The compound as claimed in claim 1 wherein said compound is selected from the group consisting of: benzylperindopril phthalic acid salt; benzylperindopril tartaric acid salt; benzylperindopril phosphate; benzylperindopril camphor suiphonate; benzylperindopril oxalate; benzylperindopril citrate; benzylperindopril (−)-di-p-toluoyl tartarate; benzylperindopril (+)-di-p-toluoyl tartarate; and benzylperindopril (±)-dibenzoyltartarate.

4. The compound of claim 3, wherein said compound is perindopril phthalic acid salt.

5. The compound of claim 3, wherein said compound is perindopril tartaric acid salt.

6. The compound of claim 3, wherein said compound is perindopril phosphate.

7. The compound of claim 3, wherein said compound is perindopril camphor sulphonate.

8. The compound of claim 3, wherein said compound is perindopril oxalate.

9. The compound of claim 3, wherein said compound is perindopril citrate.

10. The compound of claim 3, wherein said compound is perindopril-(−)-di-p-toluoyl tartarate.

11. The compound of claim 3, wherein said compound is perindopril (+)-di-p-toluoyl tartarate.

12. The compound of claim 3, wherein said compound is perindopril (±)-dibenzoyltartarate.

13. A process for preparing a compound of Formula IVA

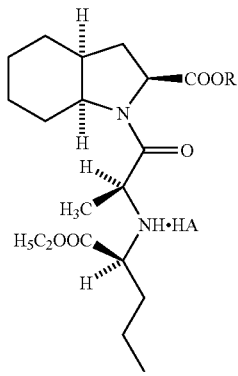

Formula IVA wherein R is selected from substituted or unsubstituted aralkyl groups, and HA represents an acid capable of forming a salt, the method comprising the step of reacting a compound of Formula IV with the acid HA

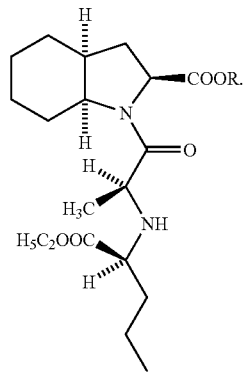

Formula IV

14. A process as claimed in claim 13, wherein the said aralkyl group is selected from the group consisting of benzyl; alkyl-substituted benzyl; alkoxy-substituted benzyl; halo-substituted benzyl; nitro-substituted benzyl; diphenyl methyl; or triphenylmethyl.

15. A process according to claim 13, wherein said compound IVA is selected from the group consisting of: benzylperindopril phthalic acid salt; benzylperindopril tartaric acid salt; benzylperindopril phosphate; benzylperindopril camphor sulphonate; benzylperindopril oxalate; benzylperindopril citrate; benzylperindopril (−)-di-p-toluoyl tartarate; benzylperindopril (+)-di-p-toluoyl tartarate; and benzylperindopril (±)-dibenzoyltartarate.

* * * * *